(12) United States Patent
Mori

(10) Patent No.: US 9,513,251 B2
(45) Date of Patent: Dec. 6, 2016

(54) GAS SENSOR

(75) Inventor: Kentaro Mori, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 493 days.

(21) Appl. No.: 12/916,994

(22) Filed: Nov. 1, 2010

(65) Prior Publication Data

US 2011/0100815 A1    May 5, 2011

(30) Foreign Application Priority Data

Nov. 2, 2009  (JP) .................................. 2009-252003
Aug. 31, 2010  (JP) .................................. 2010-193353

(51) Int. Cl.
*G01N 27/407*    (2006.01)

(52) U.S. Cl.
CPC ................................. *G01N 27/4075* (2013.01)

(58) Field of Classification Search
CPC ..................... G01N 27/4075; G01N 27/4077; G01N 27/409; G01N 27/41; G01N 33/0037
USPC ........................................................ 204/426
See application file for complete search history.

(56) References Cited

U.S. PATENT DOCUMENTS

| | | | |
|---|---|---|---|
| 6,344,119 B2* | 2/2002 | Kato et al. ..................... | 204/425 |
| 6,770,180 B1* | 8/2004 | Diehl ............................. | 204/424 |
| 2006/0185978 A1* | 8/2006 | Nagao et al. .................. | 204/424 |
| 2007/0017806 A1 | 1/2007 | Furuta et al. | |
| 2007/0246358 A1* | 10/2007 | Schneider et al. ............ | 204/424 |
| 2009/0014331 A1* | 1/2009 | Sugaya et al. ................ | 204/427 |

FOREIGN PATENT DOCUMENTS

| | | |
|---|---|---|
| JP | 2007-033114 A | 2/2007 |
| JP | 2008-14764 A | 1/2008 |

* cited by examiner

*Primary Examiner* — Louis Rufo
(74) *Attorney, Agent, or Firm* — Sughrue Mion, PLLC

(57) ABSTRACT

A gas sensor having a sensor element including: a plate-shaped solid electrolyte body; and a pair of electrodes sandwiching the electrolyte body. The electrodes include a measurement electrode portion, and a standard electrode portion disposed in an inner portion of the sensor element. A lead portion, which extends along the surface of the solid electrolyte body, is connected to the standard electrode portion. The standard electrode portion is mainly formed with a precious metal and contains a ceramic. The lead portion is mainly formed of a precious metal and has a ceramic content smaller than the standard electrode portion. A porous portion, which extends to the inner portion of the sensor element along the surface of the solid electrolyte body, has a gas permeability higher than the lead portion, is mainly formed with a ceramic, and is connected to the standard electrode portion.

11 Claims, 8 Drawing Sheets

GAS SENSOR

BACKGROUND OF THE INVENTION

1. Field of the Invention

The present invention relates to a gas sensor that includes a gas sensor element for detecting the concentration of a specific gas component in a gas to be measured. More specifically, the present invention relates to a self-generating type gas sensor in which a standard electrode functions as an oxygen standard with the accumulation of oxygen.

2. Description of the Related Art

A gas sensor of the related art includes a gas sensor element in which different magnitudes of electromotive force are generated depending on the concentration of a specific gas (for example, $NO_x$ or oxygen) in the exhaust gas of an automobile or the like. An example thereof is an oxygen sensor including an oxygen pump cell and an oxygen concentration detection cell in which a pair of electrodes sandwiches a solid electrolyte body formed of zirconia. Among them, in the oxygen pump cell, the magnitude or the direction of the current flowing between a pair of electrodes is controlled so that the electromotive force generated in the oxygen concentration detection cell becomes a standard voltage, whereby oxygen is pumped into or out of a gas detection chamber. In addition, based on the current flowing in the oxygen pump cell, the oxygen concentration of the exhaust gas and the air-fuel ratio of the exhaust gas can be detected (e.g., see Patent Document 1).

[Patent Document 1] JP-A-2007-33114

3. Problems to be Solved by the Invention

However, in the above-mentioned self-generating type gas sensor, by causing a minute current to flow in the oxygen concentration detection sensor, oxygen ions move from the detection electrode to the standard electrode, thereby accumulating oxygen in the standard electrode. In addition, a predetermined level of standard oxygen is generated in the oxygen sensor by oxygen accumulated in the standard electrode. Therefore, the standard electrode has been formed of a porous metal in which a mixed paste continuing platinum and zirconia is sintered so as to exhibit both conductivity (for providing an electrode function) and porosity (for accumulating oxygen). Furthermore, such a gas sensor includes a standard lead for electrically connecting the standard electrode with the outside and drawing oxygen, which accumulates in the standard electrode to a predetermined level or greater, to the outside. That is, since balancing the electric connection property and oxygen permeability is required even in the standard lead, the standard lead is integrally formed with a porous metal in the same manner as the standard electrode in the related art.

However, in the standard lead, as the content of the precious metal is increased so as to improve the electric connection property, the porosity and therefore the oxygen permeability decreases. On the other hand, as the content of the precious metal is decreased so as to improve the oxygen permeability and therefore increase the porosity, the electric connection property decreases. Therefore, in the gas sensor of the related art, the balance between the electric connection property and the oxygen permeability in the standard lead must be adjusted with a high degree of accuracy, whereby design of a standard lead is difficult.

SUMMARY OF THE INVENTION

The present invention has been made to solve the above-mentioned problems, and an object thereof is to facilitate the design of a standard lead of the gas sensor which otherwise would require balancing of the electric connection property and oxygen permeability.

The above object has been achieved by providing, in a first aspect of the invention, a gas sensor comprising: a sensor element configured to detect a specific gas component in a gas to be measured, the sensor element including: a plate-shaped solid electrolyte body; and a pair of electrodes that is stacked on the solid electrolyte body with the solid electrolyte body interposed therebetween, wherein the pair of electrodes includes a measurement electrode portion that is exposed to the gas to be measured, and a standard electrode portion that is disposed in an inner portion of the sensor element and functions as an oxygen standard portion through inflow of oxygen via the solid electrolyte body, wherein a lead portion, which extends in the inner portion of the sensor element along the surface of the solid electrolyte body, is connected to the standard electrode portion, wherein the standard electrode portion is formed with a precious metal as a main ingredient and contains a ceramic, wherein the lead portion is formed of a precious metal as a main ingredient and has a ceramic content (including zero) smaller than that of the standard electrode portion, and wherein a porous portion, which extends to the inner portion of the sensor element along the surface of the solid electrolyte body, has a gas permeability higher than that of the lead portion, is formed with a ceramic as a main ingredient, and is connected to the standard electrode portion.

According to the gas sensor of the first aspect of the present invention, a standard lead which requires balancing of the electric connection property and the oxygen permeability as in the related art is divided into a lead portion for securing only the electric connection property and a porous portion for securing oxygen permeability. In this manner, the design of the gas sensor element becomes easier as a result of forming lead and porous portions that are individually configured in terms of their respective function.

Furthermore, the lead portion which secures the electric connection property is formed of a precious metal as a main ingredient and has a ceramic content smaller than that of the standard electrode portion. As a result, the lead portion can be densified, whereby the electric connection property is improved.

Moreover, the less ceramic that is contained in the lead portion, the easier it is to obtain the above-mentioned effect. However, considering the close-contact property of the solid electrolyte body and the lead portion, the lead portion desirably contains ceramic in an amount of 1 wt % or more.

In the present invention, a "main ingredient" is an ingredient present in an amount of 50 wt % or more. That is, the expression "the lead portion is formed with a precious metal as a main ingredient" means that a precious metal constitutes 50 wt % or more of the ingredients of the lead portion.

To the contrary, the porous portion which secures oxygen permeability has a gas permeability higher than that of the lead portion, and is formed with a ceramic as a main ingredient. As a result, the porosity of the porous portion can be easily adjusted. For this reason, the porous portion can easily regulate the internal pressure of oxygen by regulating the flow path cross-sectional area, the flow path length and the porosity. Thus, in the porous portion, the output of the oxygen flow rate is easily regulated based on the oxygen partial pressure, which makes it possible to stabilize the oxygen flow rate.

Furthermore, the porous portion is formed with a ceramic as a main ingredient and may contain a precious metal. However, the porous portion is more preferably formed solely of a ceramic.

The expression "the gas permeability is higher than that of the lead portion" means that, when the gas to be measured flows in the standard lead and the porous portion having the same length and the same cross-sectional area under the same conditions, the outflow gas pressure of the porous portion is raised or the outflow gas velocity thereof is accelerated.

In a preferred embodiment of the gas sensor of the first aspect of the invention, the porous portion has a gas permeability higher than that of the standard electrode portion. As a result, when oxygen accumulated in the standard electrode portion is equal to or higher than a predetermined level (partial pressure), the porous portion can easily draw oxygen to the outside via the porous portion.

In another preferred embodiment of the gas sensor of the first aspect of the invention, the porous portion is stacked on the lead portion along a stacking direction of the pair of electrodes. The lead portion and the porous portion may be disposed on the solid electrolyte body in a row (along separate lines in a direction perpendicular to the stacked direction), but in this embodiment, the porous portion is stacked on the lead portion. In this manner, it is possible to easily and accurately form lead and porous portions that are individually configured in terms of their respective function.

In yet another preferred embodiment of the gas sensor according to the first aspect of the invention, the lead portion is electrically connected to an electrode pad provided on the surface of the sensor element via a through hole conductor, and a part of the porous portion communicates with an outer portion of the sensor element via a through hole provided in the through hole conductor. Generally, the standard lead provided within the sensor is electrically connected to an electrode pad provided outside the sensor element via a through hole conductor formed around an inner periphery of the through hole that is provided in the solid electrolyte body or the like. In the present invention, the porous portion communicates with the outside of the sensor element via the through-hole using the electric connection that uses the through hole conductor, whereby oxygen overflowing from the standard electrode portion can be easily discharged to the outside.

Moreover, although the porous portion communicates with the outside, if the porous portion is exposed to the through hole so that the porous portion can be seen from the outside, the above-mentioned effect can be reliably obtained and this is a more preferable configuration.

In yet another preferred embodiment of the gas sensor according to the first aspect of the invention, the precious metal is elemental platinum or an alloy of platinum with at least one selected from the group consisting of rhodium, palladium, ruthenium and gold. By using such a material, the electric connection property of the lead portion is further improved.

BRIEF DESCRIPTION OF THE DRAWINGS

Illustrative aspects of the invention will be described in detail with reference to the following drawings wherein.

DETAILED DESCRIPTION OF EXEMPLARY EMBODIMENTS OF THE PRESENT INVENTION

Hereinafter, a first embodiment of a gas sensor embodying the present invention will be described with reference to the drawings. However, the present invention should not be construed as being limited thereto.

Figure 1:
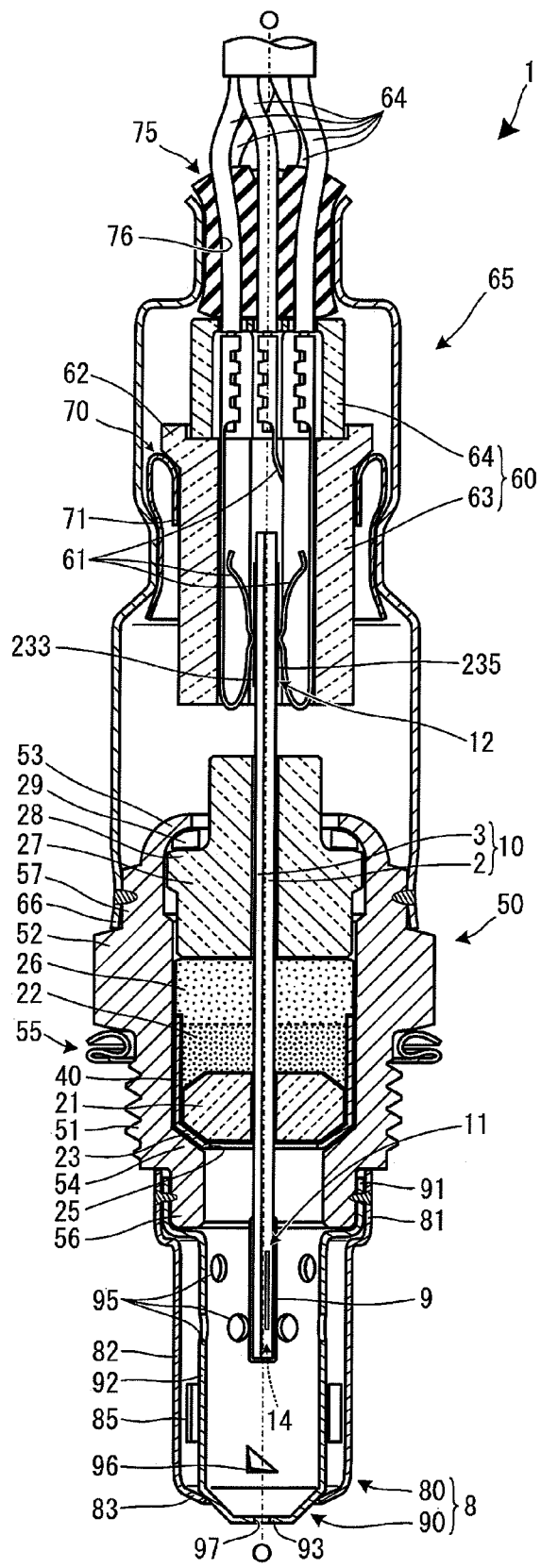
FIG. 1 is a longitudinal cross-sectional view of an oxygen sensor 1.

First, as an example of the gas sensor, an oxygen sensor 1 is adopted and a mechanical structure thereof will be described with reference to FIG. 1. In addition, an up and down direction in FIG. 1 is set as an axial O direction of the oxygen sensor 1. In addition, the description will be made by setting a lower side in FIG. 1 as a front end side of the oxygen sensor 1 and setting an upper side thereof as a rear end side.

The oxygen sensor 1 shown in FIG. 1 is an example of a full range air-fuel ratio sensor that is attached to an exhaust pipe (not shown) of an automobile and detects the concentration of oxygen (specific gas) in the exhaust gas (a gas to be measured) flowing in the discharge pipe and the air-fuel ratio of the exhaust gas.

A sensor element 10 of the oxygen sensor 1 is a plate-shaped element that extends in the axial O direction and has a narrow width, and includes a detection element 2 and a heater 3 described below (in FIG. 1, a left and right direction of the page is a plate thickness direction, and a front and rear direction is a plate width direction). Strictly speaking, "the gas sensor element" refers to the detection element 2, but, in the present invention, for convenience, the sensor element 10 in which the detection element 2 and the heater 3 are integrated with each other, is defined as "the gas sensor element" and the following description will be made. The oxygen sensor 1 has a structure in which the sensor element 10 is maintained within a metal shell 50 by disposing the sensor element 10 within a cup 40 and supporting the cup 40 within the metal shell 50. The specific structure of the sensor element 10 will be described below.

In the front end portion 11 of the sensor element 10, a detection portion 14 for detecting oxygen concentration is provided, and the detection portion 14 protrudes from an opening 25 of the front end side of the cup 40 (namely, from the front end of the metal shell 50). A front end peripheral portion 23 including the opening end of the opening 25 of the cup 40 is formed in the shape of a taper over an outer peripheral surface thereof. Within the cup 40, a ceramic ring 21 formed of alumina and a talc ring 22 which is solidified by compressing talc powder are accommodated in a state in which the sensor element 10 is inserted into its hole. The talc ring 22 is pushed into the cup 40, whereby the sensor element 10 is positioned and maintained in a position within the cup 40.

The metal shell 50 is formed of a low carbon steel such as SUS 430, and at an outer periphery front end side of the metal shell 50, an attachment portion 51 is provided in which a screw mount is formed for attaching to a discharge pipe. At a front end side from the attachment portion 51, a front end engagement portion 56 is formed which engages a protector 8 described below. In an outer periphery center of the metal shell 50, a tool engagement portion 52 is formed which engages a tool for attaching to the discharge pipe. A gasket 55 for preventing gas leakage upon attaching the gas sensor to the discharge pipe is fitted between the front end surface of the tool engagement portion 52 and the rear end of the attachment portion 51. At the rear end side of the tool engagement portion 52, a rear end engagement portion 57 engages an outer housing 65 described below, and a fastening portion 53 which fastens and maintains the sensor element 10 within the metal shell 50 at the rear end side thereof, are formed.

A step portion 54 is formed in the vicinity of the attachment portion 51 in the inner periphery of the metal shell 50. A front end peripheral portion 23 of the cup 40 that maintains the sensor element 10 is locked in the step portion 54. In the inner periphery of the metal shell 50, a talc ring 26 is loaded from the rear end side of the cup 40 in a state of having inserted the sensor element 10 therein. A tubular sleeve 27 is fitted into the metal shell 50 so as to press the talc ring 26 from the rear end side. In the rear end side outer periphery of the sleeve 27, a shoulder portion 28 having a step shape is formed. A circular fastening packing 29 is disposed on the shoulder portion 28. In this state, the fastening portion 53 of the metal shell 50 is fastened so as to press the shoulder portion 28 of the sleeve 27 toward the front end side via the fastening packing 29. The talc ring 26 pressed to the sleeve 27 is pushed within the metal shell 50 and charged within the metal shell 50.

The front end engagement portion 56 of the metal shell 50 is formed in the shape of a housing; the protector 8 is fitted to the front engagement portion 56 and is fixed by spot welding or laser welding. The protector 8 surrounds the outer periphery of the front end portion 11 of the sensor element 10 protruding from the front end of the metal shell 50, thereby protecting the sensor element 10 from damage due to vibration or physical impact. The protector 8 has a double structure which includes a housing-shaped inner protector 90 with a bottom, and a housing-shaped outer protector 80 surrounding the inner protector 90 in the radial direction so as to define a gap between the inner and outer protectors.

In the inner protector 90, a plurality of inner introduction holes 95 open to a rear end side of a peripheral wall 92, a plurality of water drain holes 96 open to a front end side of the peripheral wall 92, and an exhaust hole 97 opens at a bottom wall 93. In addition, a proximal end portion 81 of an opening end side (a rear end side) engages the outer periphery of the front end engagement portion 56. In the outer protector 80, a plurality of outer introduction holes 85 open to the front end side of the peripheral wall 82. A proximal end portion 81 of the opening end side engages the outer periphery of the proximal end portion 91 of the inner protector 90. In addition, the front end portion 83 of the outer protector 80 is bent inwardly toward the peripheral wall 92 of the inner protector 90 so as to close the gap between the outer protector 80 and the inner protector 90.

The rear end portion 12 of the sensor element 10 protrudes from the rear end (the fastening portion 53) of the metal shell 50, and on the surface of the rear end portion 12, electrode pads 231 to 235 (see FIGS. 2 and 3) electrically connecting the detection element 2 or the heater 3 to respective connection terminals 61 are formed (the electrode pads 233 and 235 among them are shown in FIG. 1). In addition, the rear end portion 12 is covered with a housing-shaped separator 60 formed of an insulative ceramic. The separator 60 houses five connection terminals 61 (three terminals among them are shown in FIG. 1) which are brought into contact with (electrically connected to) each of the electrode pads 231 to 235. The separator 60 includes a front end side separator 63 and a rear end side separator 64, and the front end of the rear end side separator 64 engages an edge portion 62 provided at the rear end of the front end side separator 63. The front end side separator 63 is accommodated in a state in which five connection terminals 61 are disposed so as not to come into electrical contact with one another. In the rear end side separator 64, five lead lines (not shown) to be withdrawn to the outside of the oxygen sensor 1 are accommodated in a state of being disposed so as not to come into contact with one another.

The outer housing 65 is a member having a housing shape made of stainless steel (e.g., SUS304) and covers and protects the rear end portion 12 of the sensor element 10 or the surroundings of the separator 60. The opening portion 66 of the front end side of the outer housing 65 engages the outer periphery of the rear end engagement portion 57 of the metal shell 50, so that the outer housing 65 is fastened from the outer periphery side and laser-welded to the rear end engagement portion 57 over its entire periphery.

A maintenance fitting 70 is installed in the gap between the outer housing 65 and the front end side separator 63. The maintenance fitting 70 has a housing shape made of metal and has a support portion 71 in which the rear end thereof is bent to the inside. The maintenance fitting 70 locks the edge portion 62 of the front end side separator 63, which is inserted into the inner portion thereof, to the support portion 71, thereby supporting the front end side separator 63. In this state, the outer peripheral surface of the outer housing 65 of a portion where the maintenance fitting 70 is disposed is fastened and the maintenance fitting 70 supporting the front end side separator 63 is fixed to the outer housing 65.

A grommet 75 made of a fluorine-based rubber is fitted in the opening of the rear end side of the outer housing 65. The grommet 75 has five insertion holes 76 (three of these holes are shown in FIG. 1), and five lead lines (not shown) withdrawn from the rear end side separator 64 are inserted into each insertion hole 76 in an airtight manner.

Figure 2:
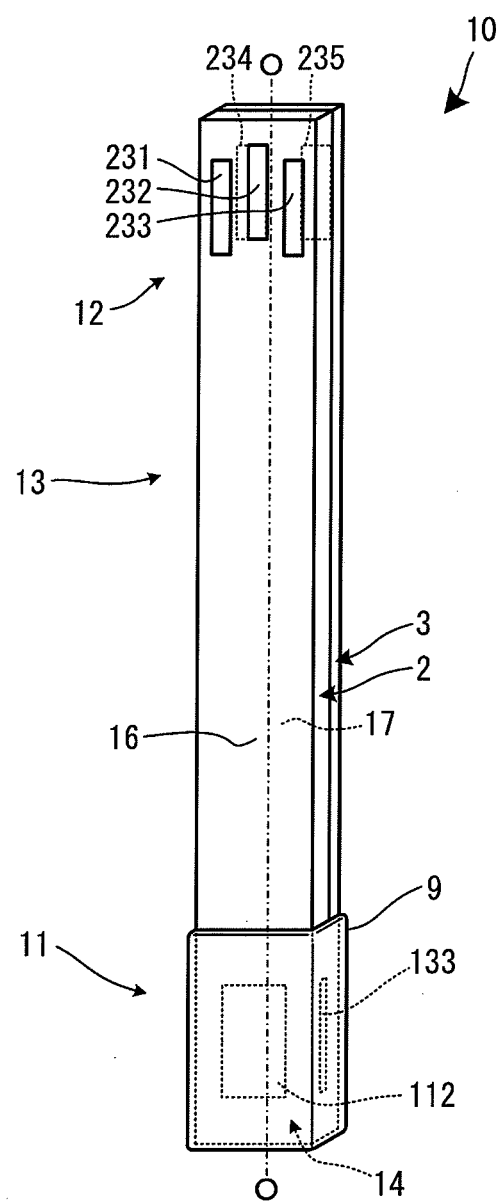
FIG. 2 is a perspective view showing an exterior of the sensor element 10.

Next, the configuration of the sensor element 10 will be described with reference to FIG. 2. Furthermore, in FIG. 2, the up and down directions refer to the axial O direction of the sensor element 10, respectively. In addition, in the description of FIG. 2, the lower side thereof refers to the front end side of the sensor element 10, and the upper side thereof refers to the rear end side of the sensor element 10. The sensor element 10 shown in FIG. 2 is an element in which the detection element 2 formed in a plate shape with the thin width extending in the axial O direction and the heater 3 are stacked in the thickness direction and integrated with one another. In the detection portion 14 positioned at the front end side of the sensor element 10, a gas detection chamber 132 is provided (see FIG. 3) for introducing the exhaust gas therein and detecting the oxygen concentration in the exhaust gas. Furthermore, in order to protect the detection portion 14 from contamination due to a deposit (adhesive matter causing pollution, such as fuel ash or an oil component) in the exhaust gas, the detection portion 14 is covered with the porous protective layer 9.

In the rear end portion 12 of the sensor element 10, among the outer surfaces perpendicular to the thickness direction thereof, in the outer surface (hereinafter, referred to as a "main surface") 16 of the detection element 2 side, the electrode pads 231, 232 and 233 are formed. The electrode pads 231, 232 and 233 come into contact with three of five connection terminals 61 (see FIG. 1) of the separator 60, respectively, and are electrically connected thereto. Similarly, on the outer surface (hereinafter, referred to as "rear surface") 17 of the heater 3 side opposite the main surface 16 in the thickness direction, the electrode pads 234 and 235 are formed. The electrode pads 234 and 235 come into contact with the remaining two connection terminals 61, respectively, and are electrically connected thereto.

Figure 3:
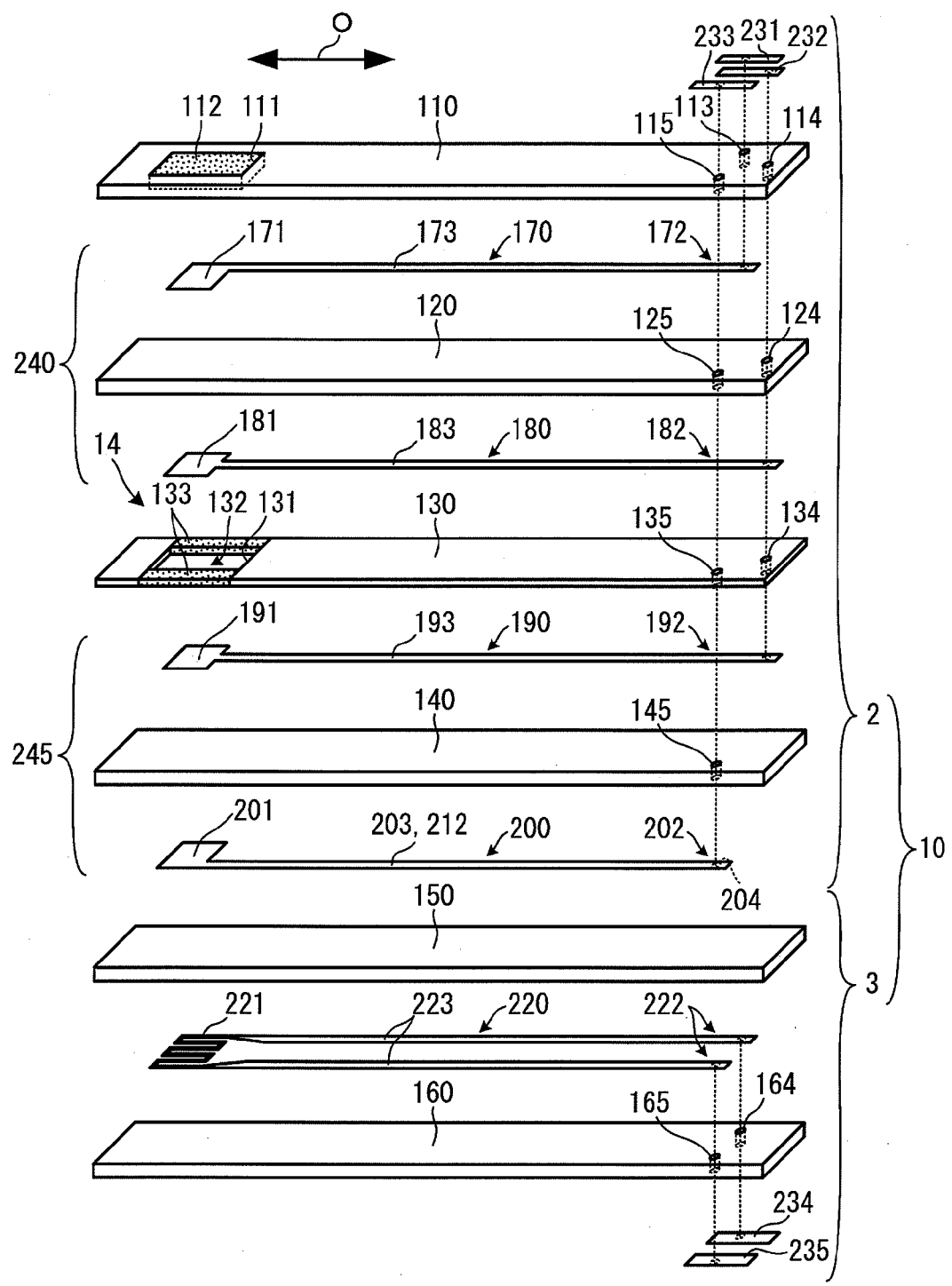
FIG. 3 is an exploded perspective view of the sensor element 10 in a first embodiment.

Next, the inner structure of the sensor element 10 will be described in detail with reference to FIG. 3. Furthermore, in FIG. 3, the left and right directions refer to the axial O direction of the sensor element 10, respectively. In addition, in the description of FIG. 3, the left side refers to the front end side of the sensor element 10, and the right side refers to the rear end side of the sensor element 10. Furthermore, the outer surface of each member to be disposed on the main surface 16 side (an upper side of FIG. 3) of the sensor element 10 is referred to as a "main surface" similar to the sensor element 10, and the outer surface of each member to be disposed on the rear surface 17 side (a paper lower side of FIG. 3) is similarly referred to as a "rear surface".

The sensor element 10 is configured such that the detection element 2 and the heater 3 are stacked on each other. The detection element 2 has a structure in which insulation base bodies 110 and 130 formed of alumina having an insulating property as the main body and solid electrolyte bodies 120 and 140 formed of zirconia as the main body are stacked from the main surface 16 side to the rear surface 17 side in the order of the insulation base body 110, the solid electrolyte body 120, the insulation base body 130, and the solid electrolyte body 140. On each of both surfaces of the solid electrolyte body 120 and the solid electrolyte body 140, a pair of electric current conduction patterns 170 and 180 and a pair of electric current conduction patterns 190 and 200 are formed, respectively. Each of the insulation base bodies 110 and 130 and each of the solid electrolyte bodies 120 and 140 are formed as plate bodies having thin widths of substantially the same size.

The solid electrolyte bodies 120 and 140 are constituted by a partially stabilized sintered zirconia body that is formed by adding yttria or calcia as a stabilizer to zirconia. The solid electrolyte bodies 120 and 140 contain 10 to 80 wt % of alumina in zirconia in which yttria is added as a stabilizer.

The insulation base bodies 110 and 130 and insulation base bodies 150 and 160 described below are not particularly limited to a sintered ceramic body, but, as a ceramic, for example, alumina, spinel, mullite, zirconia or the like can be used. One kind of ceramic can be used, or two kinds thereof can also be used in combination. In this embodiment, the insulation base bodies 110, 130, 150 and 160 are ceramic sintered bodies formed with alumina as the main body.

The electric current conduction patterns 170, 180 and 190 and a heating resistor 220 can be formed of platinum group elements. Useful platinum group elements include platinum, rhodium, palladium and the like. One kind thereof can be used alone, and two or more kinds can be used in combination. In this embodiment, the electric current conduction patterns 170, 180 and 190 and the heating resistor 220 are formed of platinum that has excellent heat-resistance and oxidation-resistance as the main body.

In the electric current conduction pattern 200, since an electrode portion 201 functions as an oxygen standard portion described below, at least the electrode portion 201 is constituted by a porous metal containing a precious metal so as to have both conductivity (the electric connection property) for providing an electrode function and porosity (oxygen permeability) for accumulating oxygen. As the precious metal, elemental platinum or an alloy of platinum with at least one selected from rhodium, palladium, ruthenium and gold can be used. As the precious metal, platinum having excellent heat-resistance and oxidation-resistance is desirable. However, in the electric current conduction pattern 200 of the present embodiment, a configuration in which a porous portion 212 is stacked on a lead portion 203 is used, and the details thereof are described below.

Furthermore, the electric current conduction patterns 170, 180, 190 and 200 and the heating resistor 220 comprising a precious metal as a main ingredient may include a ceramic ingredient. The ceramic ingredient is included to secure the fixing (adhering) strength of the respective electric current conduction patterns 170, 180, 190 and 200, the heating resistor 220, and the insulation base bodies 110, 130, 150 and 160 into which the ceramic is introduced. The ceramic ingredient desirably has the same ingredients as those which form the main body of the insulation base bodies 110, 130, 150 and 160 into which the respective electric current conduction patterns 170, 180, 190 and 200 and the heating resistor 220 are respectively embedded, from the viewpoint of enhancing the fixing strength.

The electric current conduction pattern 170 that is formed on the main surface of the solid electrolyte body 120 has a lead portion 173 extending from the front end side (the left side in the drawings) of the solid electrolyte body 120 to the rear end side (the right side in the drawings) thereof. An electrode portion 171 having a wide width is formed at the front end side of the lead portion 173. The insulation base body 110 is stacked on the main surface side of the solid electrolyte body 120, and the electric current conduction pattern 170 is sandwiched therebetween. At the rear end side of the insulation base body 110, in a position corresponding to that of the rear end portion 172 of the electric current conduction pattern 170, a through hole 113 is formed. On the main surface of the insulation base body 110 becoming the main surface 16 of the sensor element 10, in the position of the rear end side corresponding to the through hole 113, an electrode pad 231 is formed. The electrode pad 231 is electrically connected to the rear end portion 172 of the electric current conduction pattern 170 via a through hole conductor formed in the through hole 113.

At the front end side of the insulation base body 110, in the position where the electrode portion 171 is disposed, an opening portion 111 is provided penetrating in the thickness direction of the insulation base body 110. In the opening portion 111, a porous layer 112 having a porous texture formed of alumina as a main body is provided. The electrode portion 171 of the electric current conduction pattern 170 is configured so as to communicate with the air via the porous layer 112.

On the rear surface of the solid electrolyte body 120, the electric current conduction pattern 180 facing the electric current conduction pattern 170 is formed. Similar to the electric current conduction pattern 170, the electric current conduction pattern 180 has a lead portion 183 extending from the front end side of the solid electrolyte body 120 to the rear end side thereof, and an electrode portion 181 formed so that the width thereof is widened in the front end side of the lead portion 183. The electrode portion 181 is disposed at a position facing the electrode portion 171 of the electric current conduction pattern 170 with the solid electrolyte body 120 sandwiched therebetween. A pair of electrode portions 171 and 181 sandwiching the solid electrolyte body 120 and the solid electrolyte body 120 function as an oxygen pump cell (hereinafter, also referred to as an "IP cell") 240 that pumps oxygen into and out of the chamber 132. At the rear end side of the solid electrolyte body 120 and the insulation base body 110, in the position corresponding to the rear end portion 182 of the electric current conduction pattern 180, a through hole 124 and a through hole 114 are formed, respectively. On the main surface of the rear end side of the insulation base body 110, in a position corresponding to the through hole 114, an electrode pad 232 is formed. The electrode pad 232 is disposed on the main surface of the rear end side of the insulation base body 110 in a position parallel to the electrode pad 231 in the width direction. The electrode pad 232 is electrically connected to the rear end portion 182 of the electric current conduction pattern 180 via a through hole conductor formed in the through hole 114 and a through hole conductor formed in the through hole 124.

At the rear surface side of the solid electrolyte body 120, the insulation base body 130 is stacked so as to sandwich the electric current conduction pattern 180 between the insulation base body 130 and the solid electrolyte body 120. At the front end side of the insulation base body 130, even at a position where the electrode portion 181 of the electric current conduction pattern 180 is disposed, an opening portion 131 is formed passing through the thickness direction thereof. The opening portion 131 is closed by the solid electrolyte body 120 and the solid electrolyte body 140 that are stacked and disposed on the thickness direction side of the insulation base body 130, and the inner portion thereof is constituted by the gas detection chamber 132. The electrode portion 181 of the electric current conduction pattern 180 is disposed within the gas detection chamber 132.

A diffusion rate limiting portion 133 is provided in the side wall of the opening portion 131, in side walls of the width direction of both sides of the insulation base body 130. The diffusion rate limiting portion 133 is formed as a porous body from alumina, and configured such that the exhaust gas surrounding the sensor element 10 is introduced into the gas detection chamber 132 via the diffusion rate limiting portion 133. The diffusion rate limiting portion 133 is provided to limit the inflow amount of exhaust gas into the gas detection chamber 132.

The solid electrolyte body 140 is stacked at the rear surface side of the insulation base body 130. On the main surface of the solid electrolyte body 140, in a manner similar to the electric current conduction patterns 170 and 180, the electric current conduction pattern 190 is formed, which has a lead portion 193 extending from the front end side of the solid electrolyte body 140 to the rear end side thereof and an electrode portion 191 of increased width at the front end side of the lead portion 193. The electrode portion 191 of the electric current conduction pattern 190 is also exposed to the gas detection chamber 132. A through hole 134 is formed at the rear end side of the insulation base body 130, in a position corresponding to the rear end portion 192 of the electric current conduction pattern 190. The forming position of the through hole 134 also corresponds to the forming position of the rear end portion 182 of the electric current conduction pattern 180 of the main surface side of the insulation base body 130. The rear end portion 182 of the electric current conduction pattern 180 and the rear end portion 192 of the electric current conduction pattern 190 are electrically connected to each other via a through hole conductor formed in the through hole 134. That is, the electric current conduction pattern 180, the electric current conduction pattern 190 and the electrode pad 232 are electrically connected with each other.

The electric current conduction pattern 200 facing the electric current conduction pattern 190 is also formed on the rear surface of the solid electrolyte body 140. In a manner similar to the electric current conduction pattern 190, the electric current conduction pattern 200 has a lead portion 203 extending from the front end side of the solid electrolyte body 140 to the rear end side thereof, and an electrode portion 201 of increased width at the front end portion of the lead portion 203. The electrode portion 201 is disposed at a position facing the electrode portion 191 of the electric current conduction pattern 190 with the solid electrolyte body 140 sandwiched therebetween. A pair of the electric current conduction patterns 190 and 200 (specifically, a pair of electrode portions 191 and 201) sandwiching the solid electrolyte body 140 therebetween and the solid electrolyte body 140 function as the oxygen concentration detection cell (hereinafter, also referred to as a "VS cell") 245.

An electrode pad 233 is formed parallel to the electrode pad 231 and the electrode pad 232 on the main surface of the rear end side of the insulation base body 110. The arrangement position of the rear end portion 202 of the electric current conduction pattern 200 corresponds to the forming position of the electrode pad 233 in the thickness direction. The through holes 115, 125, 135 and 145 which continuously penetrate in the thickness direction are respectively formed in the insulation base body 110, the solid electrolyte body 120, the insulation base body 130 and the solid electrolyte body 140 which are interposed between the rear end portion 202 of the electric current conduction pattern 200 and the electrode pad 233. In addition, the rear end portion 202 of the electric current conduction pattern 200 and the electrode pad 233 are electrically connected to each other via through hole conductors formed in the through holes 115, 125, 135 and 145.

The configuration of the heater 3 will next be described. The heater 3 has a structure in which a heating resistor 220 is sandwiched between the rear surface of an insulation base body 150 formed of alumina having an insulating property as the main ingredient and the main surface of the insulation base body 160. The heating resistor 220 includes one conductor pattern connected within the heater 3 and has a heating portion 221 including a pattern having a small cross-sectional area so that heating is mainly performed at the heating portion 221. The heating portion 221 is installed in the front end portion 11 (see FIG. 2, the left side in FIG. 3) of the sensor element 10. Two lead portions 223, which are connected to both ends of the heating portion 221 respectively, have cross-sectional areas greater than the heating portion 221 and extend to the rear end side (the right side in FIG. 3) of the insulation base bodies 150 and 160 along the axial O direction. Further, the two lead portions 233 are arranged in a row in the width direction.

Two electrode pads 234 and 235 arranged in the width direction of the insulation base body 160 are provided on the rear surface of the insulations base body 160, at the rear end side thereof. The electrode pads 234 and 235 are each electrically connected to the rear end portions 222 of the two lead portions 233 of the heating resistor 220 via the through hole conductors which are formed in two through holes 164 and 165, respectively.

Herein, an operation of detecting the oxygen concentration (the air-fuel ratio of the exhaust gas) of a gas to be detected using the oxygen sensor 1 is briefly described below. Firstly, a minute current is conducted from the electrode portion 201 of the VS cell 245 toward the electrode portion 191. By means of the electric current conduction, oxygen in the gas to be detected is transferred from the electrode portion 191 side to the electrode portion 201 side via the solid electrolyte body 140, whereby the electrode portion 201 functions as an oxygen standard portion. Next, the electromotive force Vs generated between the electrode portions 191 and 201 is detected, and the magnitude or the direction of the pump current Ip flowing between the electrode portions 171 and 181 of the IP cell 240 is controlled so that the electromotive force Vs becomes a standard voltage. In addition, the oxygen concentration contained in the gas to be detected and the air-fuel ratio of the exhaust gas is specified based on the magnitude and the direction of the pump current Ip that is output from the oxygen sensor 1.

Next, the specific structure of the electric current conduction pattern 200 according to the present embodiment will be described with reference to FIGS. 4 and 5. The upper and lower surfaces of the electric current conduction pattern 200 shown in FIGS. 4 and 5 are reversed in reference to the configuration shown in FIG. 3 for convenience of explanation.

Figure 4:
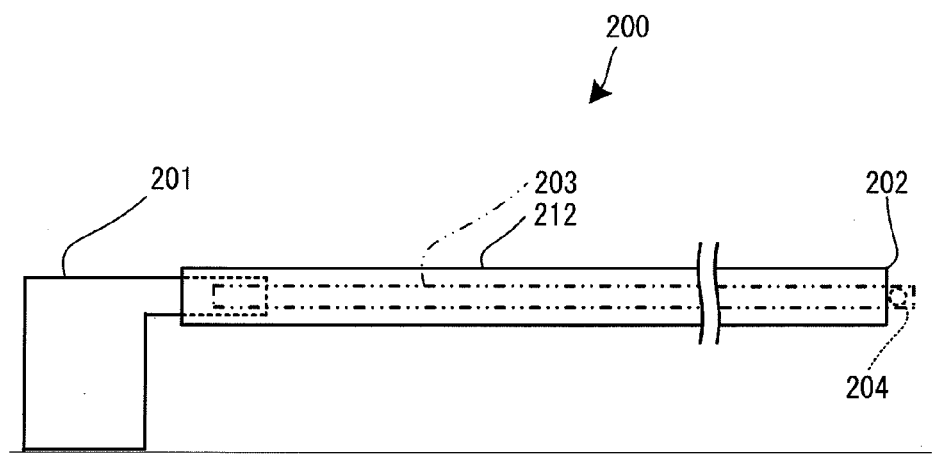
FIG. 4 is a plan view of an electric current conduction pattern 200 seen from a rear side.
Figure 5:
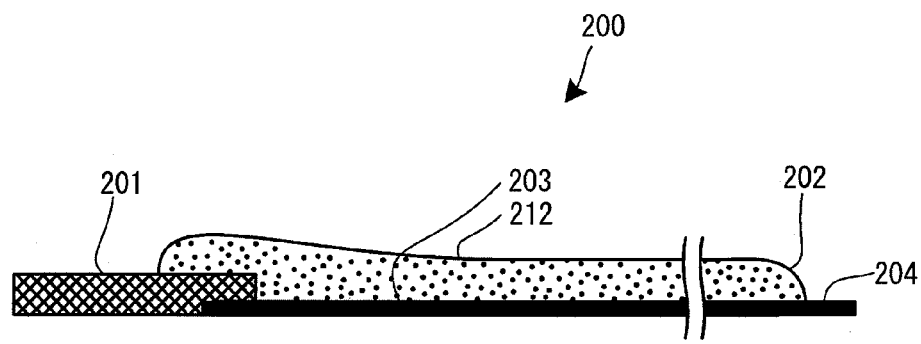
FIG. 5 is a longitudinal cross-sectional view of the electric current conduction pattern 200 shown in FIG. 4.

As shown in FIGS. 4 and 5, the electric current conduction pattern 200 of the present embodiment has a one layer structure in which the electrode portion 201 has both an electric connection property and oxygen permeability. On the other hand, the lead portion 203 is formed only for securing an electric connection; and the porous portion 212 for securing an oxygen permeability is stacked on the lead portion 203. The rear end side of the electrode portion 201 is connected to and sandwiched by the front end side of the lead portion 203 and the porous portion 212. In the present embodiment, the thickness of the electrode portion 201 is 30 μm. On the other hand, the thickness of the lead portion 203 is 10 μm, and the thickness of the porous portion 212 is 50 μm.

The electrode portion 201 is constituted as a porous metal in which a paste having a ceramic ingredient mixed with a precious metal is sintered. Herein, the electrode portion 201 is a sintered body in which alumina in an amount of 14 wt % is mixed with platinum. The sintering of platinum contained in the paste is hindered by the alumina and the porosity increases, whereby the sintered body suitably exhibits both conductivity and a porous property. As a result, the electrode portion 201 not only functions as the electrode, but also accumulates oxygen in the gas to be detected which is transferred via the solid electrolyte body 140 and functions as the oxygen standard portion.

The lead portion 203 has an electric resistance that is smaller than that of the electrode portion 201, and, for example, the electric resistance with respect to the same volume of the electrode portion 201 is equal to or less than ⅕. Namely, the lead portion 203 is formed with a precious metal as a main ingredient and hardly contains a ceramic ingredient (or contains no ceramic at all). Furthermore, the content (in wt %) of the ceramic ingredient is equal to or less than ⅓ that of the electrode portion 201. Herein, the lead portion 203 is the sintered body of the paste in which alumina in an amount of 3.5 wt % is mixed with platinum. Due to the small content of the ceramic ingredient, the sintering of platinum contained in the paste sufficiently progresses and the porosity decreases. As a result, the lead portion 203 is superior to the electrode portion 201 in conductivity (i.e., electric connection property), thereby electrically connecting the electrode portion 201 and the rear end portion 202.

The porous portion 212 has a porosity higher than that of the electrode portion 201, and is a ceramic sintered body in which a paste containing a pore forming material mixed with a ceramic is sintered. The porous portion 212 of the present embodiment is a sintered body of the paste in which carbon is mixed with alumina or zirconia, and the porosity thereof is 30 to 50 volume %. As a result, the porous portion 212 is superior to the lead portion 203 in terms of the porous property (i.e., oxygen permeability). Further, the porous portion 212 causes oxygen overflowing from the electrode portion 201 which is in an oxygen saturation state to escape to the rear end portion 202, and which would otherwise disturb the electric connection due to the insulating property.

Moreover, the rear end side of the electrode portion 201 is covered by the front end side of the porous portion 212, while the electrode portion 201 covers the front end side of the lead portion 203. This is because the lead portion 203 has the smallest porosity, and the porosity is heightened in the order of the electrode portion 201 and the porous portion 212. For example, in the case of forming the lead portion 203 on the porous portion 212, the lead portion 203 would penetrate the porous portion 212 and the porosity of the porous portion 212 would decrease, whereby the oxygen permeability would consequently decrease as well. To the contrary, by forming the lead portion 203, the electrode portion 201 and the porous portion 212 in this order, it is possible to maintain the oxygen permeability of the electrode portion 201 and the porous portion 212.

Furthermore, the lead portion 203 and the porous portion 212 extend, respectively, in the rear end portion 202 of the electric current conduction pattern 200. Further, the lead portion 203 is connected to a through hole conductor provided in the through hole 145 by a through hole connection body 204 situated at the main surface side of the rear end portion 202. As a result, the electrode portion 201 and the electrode pad 233 are electrically connected to each other via the through hole 145. Furthermore, the porous portion 212 communicates with the through hole 145, whereby it is possible to cause oxygen overflowing from the electrode portion 201 to escape to the outside of the sensor element 10 via the through hole 145.

The electric current conduction pattern 200 can be made using the production process (see JP-A-2008-14764 or the like) of a known gas sensor element, and may be installed in the sensor element 10. For example, in the electrode forming process, according to a known screen printing technique, at the rear surface side of an unbaked solid electrolyte body (not shown) becoming the solid electrolyte body 140 after baking, firstly, an unbaked lead portion (not shown) becoming the lead portion 203 after baking is formed. Next, unbaked electrodes (not shown) becoming the electrode portions 201 after baking are respectively formed so that a part thereof overlaps the front end side of the unbaked lead portion becoming the lead portion 203 after baking. In addition, an unbaked porous portion (not shown) becoming the porous portion 212 after baking is formed so as to cover an unbaked lead portion (not shown) becoming the lead portion 203 after baking.

As described above, in the oxygen sensor 1 of the present embodiment, a two layer structure was adopted in which a lead portion 203 for securing only electric connection and a porous portion 212 for securing oxygen permeability are stacked. In this manner, by adopting the stacked structure in which the lead portion 203 and a porous portion 212 are functionally divided, the design and the formation of the sensor element 10 is facilitated.

Furthermore, the lead portion 203 which secures only electric connection is formed with platinum as a main ingredient and has an alumina (more generally, a ceramic) content lower than that of the electrode portion 201. As a result, the lead portion 203 can be densified and the electric connection property is improved.

To the contrary, the porous portion 212 which secures oxygen permeability is formed of alumina and has a gas permeability higher than that of the lead portion 203. As a result, the porous portion 212 can easily regulate the internal pressure of oxygen in the porous portion 212 by regulating the flow path cross-sectional area thereof and the porosity. That is, the output regulation of the oxygen flow rate is facilitated based on the oxygen partial pressure, whereby it is possible to stabilize the oxygen flow rate.

Furthermore, in the oxygen sensor 1 of the first embodiment, the porous portion 212 has a gas permeability that is higher than that of the electrode portion 201. As a result, when oxygen accumulating in the electrode portion 201 is equal to or higher than a predetermined level (partial pressure), the excess oxygen can be easily drawn to the outside via the porous portion 212.

Furthermore, in the oxygen sensor 1 of the first embodiment, the porous portion 212 is stacked on the lead portion 203. In this manner, it becomes possible to easily and accurately form a lead portion 203 and a porous portion 212 that are individually configured in terms of their respective functions.

Moreover, in the oxygen sensor 1 of the first embodiment, the lead portion 203 is electrically connected to the electrode pad 233 via a through hole conductor, and a part of the porous portion 212 communicates with the outer part of the sensor element 10 via the through holes 115, 125, 135 and 145 provided within the through hole conductor. As a result, it is possible to easily discharge oxygen overflowing from the electrode portion 201.

Next, a second embodiment of the gas sensor element of the present invention will be described with reference to the drawings. As noted above, the present invention should not be construed as being limited thereto.

In the present (second) embodiment, in a manner similar to the first embodiment, as an example of the gas sensor element, the sensor element 10 of the oxygen sensor 1 is adopted, but the mechanical structure thereof is basically the same as that indicated in the first embodiment. Hereinafter, the same structural features as in the first embodiment are denoted by the same reference numerals, and only differences from the first embodiment will be described.

Figure 6:
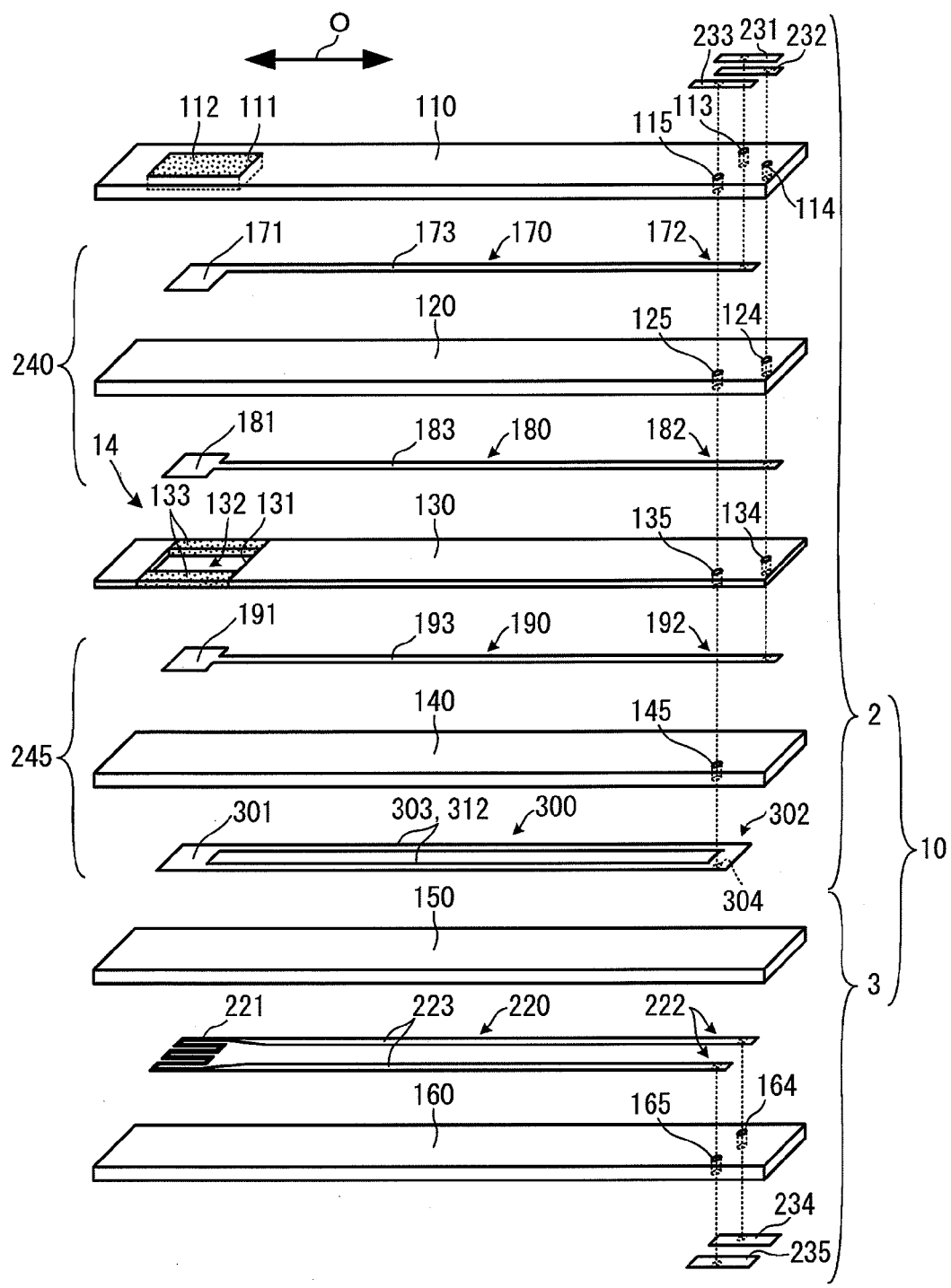
FIG. 6 is an exploded perspective view of a sensor element 10 in a second embodiment.

As shown in FIG. 6, in the sensor element 10 of the oxygen sensor 1 according to the second embodiment, a pair of electric current conduction patterns 190 and 300 sandwiching the solid electrolyte body 140 therebetween is formed. The electric current conduction pattern 300 of the present embodiment is basically the same as the electric current conduction pattern 200 according to the first embodiment except that the lead portion 303 and the porous portion 312 are arranged in parallel and a rear end portion 302 is provided. The details thereof are described below.

The electric current conduction pattern 300 has a lead portion 303 extending from the front end side of the solid electrolyte body 140 to the rear end side thereof, an electrode portion 301 which is formed to have a wide width in the front end portion of the lead portion 303, and a rear end portion 302 which is formed to have substantially the same width as the electrode portion 301 at the rear end side of the lead portion 303. The electrode portion 301 is disposed at a position facing the electrode portion 191 of the electrode conduction pattern 190 with the solid electrolyte body 140 sandwiched therebetween. A pair of electric current conduction patterns 190 and 300 (specifically, a pair of electrode portions 191 and 301) sandwiching the solid electrolyte body 140 therebetween and the solid electrolyte body 140 function as the Vs cell 245. Furthermore, the rear end portion 302 of the electrode conduction pattern 300 and the electrode pad 233 are configured so as to be electrically connected with each other via the through hole conductors formed in the through holes 115, 125, 135 and 145.

Next, a specific structure of the electrode conduction pattern 300 according to the present embodiment will be described with reference to FIGS. 7 and 8. Moreover, the upper and lower surfaces of the electrode conduction pattern 300 shown in FIGS. 7 and 8 are reversed in reference to the configuration shown in FIG. 6 for convenience of explanation.

Figure 7:
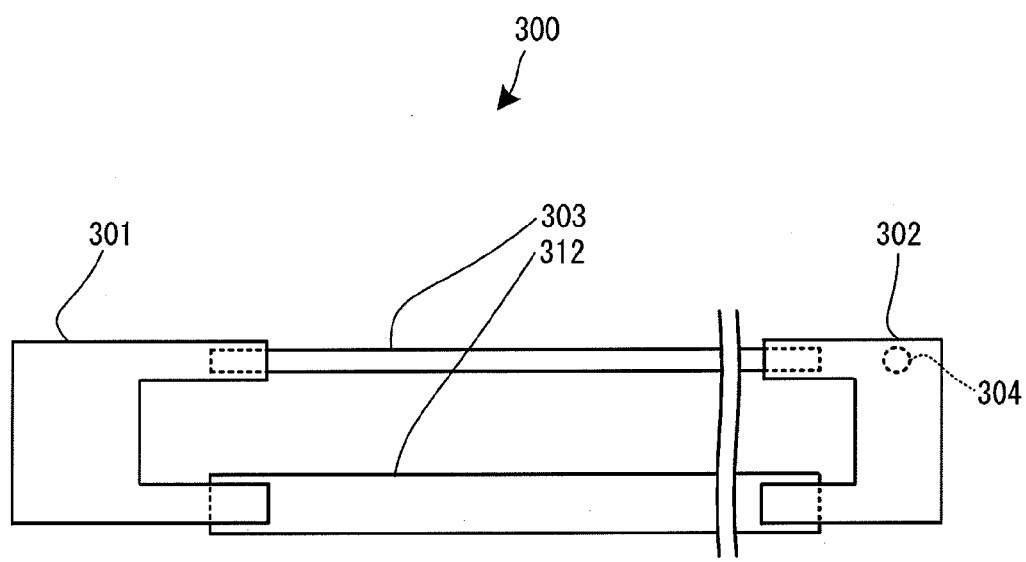
FIG. 7 is a plane view of an electric current conduction pattern 300 seen from a rear side.
Figure 8:
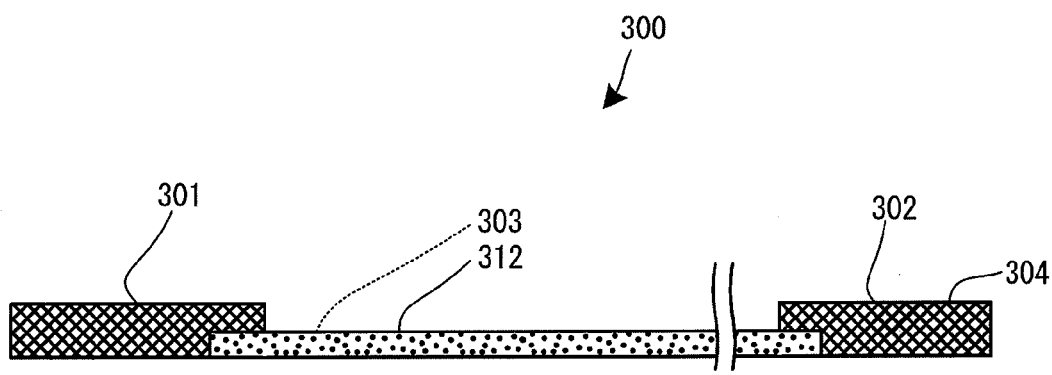
FIG. 8 is a longitudinal cross-sectional view of the electric current conduction pattern 300 shown in FIG. 7.

As shown in FIGS. 7 and 8, in the electrode conduction pattern 300 according to the present embodiment, the electrode portion 301 and the rear end portion 302 have a single layer structure exhibiting both an electric connection property and oxygen permeability. On the other hand, the lead portion 303 for securing only electric connection and the porous portion 312 for securing oxygen permeability form a two row structure extending in the left and right directions (the up and down direction in FIG. 7). That is, the porous portion 312 is separated from the lead portion 303 and is connected to the rear end side of the electrode portion 301 and the front end side of the rear end portion 302. Furthermore, in the present embodiment, the thicknesses of the electrode portion 301, the rear end portion 302, the lead portion 303, and the porous portion 312 are all substantially 30 μm.

Furthermore, as shown in FIG. 7, the front end side and the rear end side of the lead portion 303 are covered by the rear end side of the electrode portion 301 and the rear end portion 302. This is because the lead portion 303 has a porosity smaller than that of the electrode portion 301 or the rear end portion 302. For example, in the case where the lead portion 303 is formed on the electrode portion 301 or the rear end portion 302, the lead portion 303 penetrates the electrode portion 301 or the rear end portion 302, the porosity of the electrode portion 301 or the rear end portion 302 declines, and the oxygen permeability declines. To the contrary, the electrode portion 301 and the rear end portion 302 are formed on the lead portion 303, whereby it is possible to maintain the oxygen permeability of the electrode portion 301 and the rear end portion 302.

Furthermore, as shown in FIG. 7, the front end side and the rear end side of the porous portion 312 cover the rear end side of the electrode portion 301 and the rear end portion 302. This is because the porous portion 312 has a greater porosity than the electrode portion 301 or the rear end portion 302. For example, in the case where the electrode portion 301 or the rear end portion 302 is formed on the porous portion 312, the electrode portion 301 or the rear end portion 302 penetrates the porous portion 312, the porosity of the porous portion 312 declines, and the oxygen permeability thereof declines. To the contrary, the porous portion 312 is formed on the electrode portion 301 and the rear end portion 302, whereby it is possible to maintain the oxygen permeability of the porous portion 312.

In the sensor element 10 of the oxygen sensor 1 of the above-mentioned embodiment, the solid electrolyte body 140 corresponds to the "solid electrolyte body" of the present invention. The electrode portions 191 and 201 and the electrode portions 191 and 301 correspond to "a pair of electrodes" of the present invention, respectively. The electrode portion 191 corresponds to the "measurement electrode portion" of the present invention, and the electrode portions 201 and 301 correspond to the "standard electrode portion" of the present invention, respectively. The lead portions 203 and 303 correspond to the "lead portion" of the present invention. The porous portions 212 and 312 correspond to the "porous portion" of the present invention. The through holes 115, 125, 135 and 145 correspond to the "through hole" of the present invention.

Moreover, the present invention is not limited to the embodiments described above, and various modifications in form and detail of the invention can be made within the spirit and scope of the claims appended hereto.

For example, in the second embodiment, the porous portion 312 communicates with the through holes 115, 125, 135 and 145 in which the through hole conductors, which are electrically connected to the rear end portion 302 of the electrode conduction pattern 300, are formed, but the present invention is not limited thereto. Hereinafter, a modified example of the sensor element 10 of the oxygen sensor 1 according to the second embodiment will be described with reference to FIGS. 9 and 10.

Figure 9:
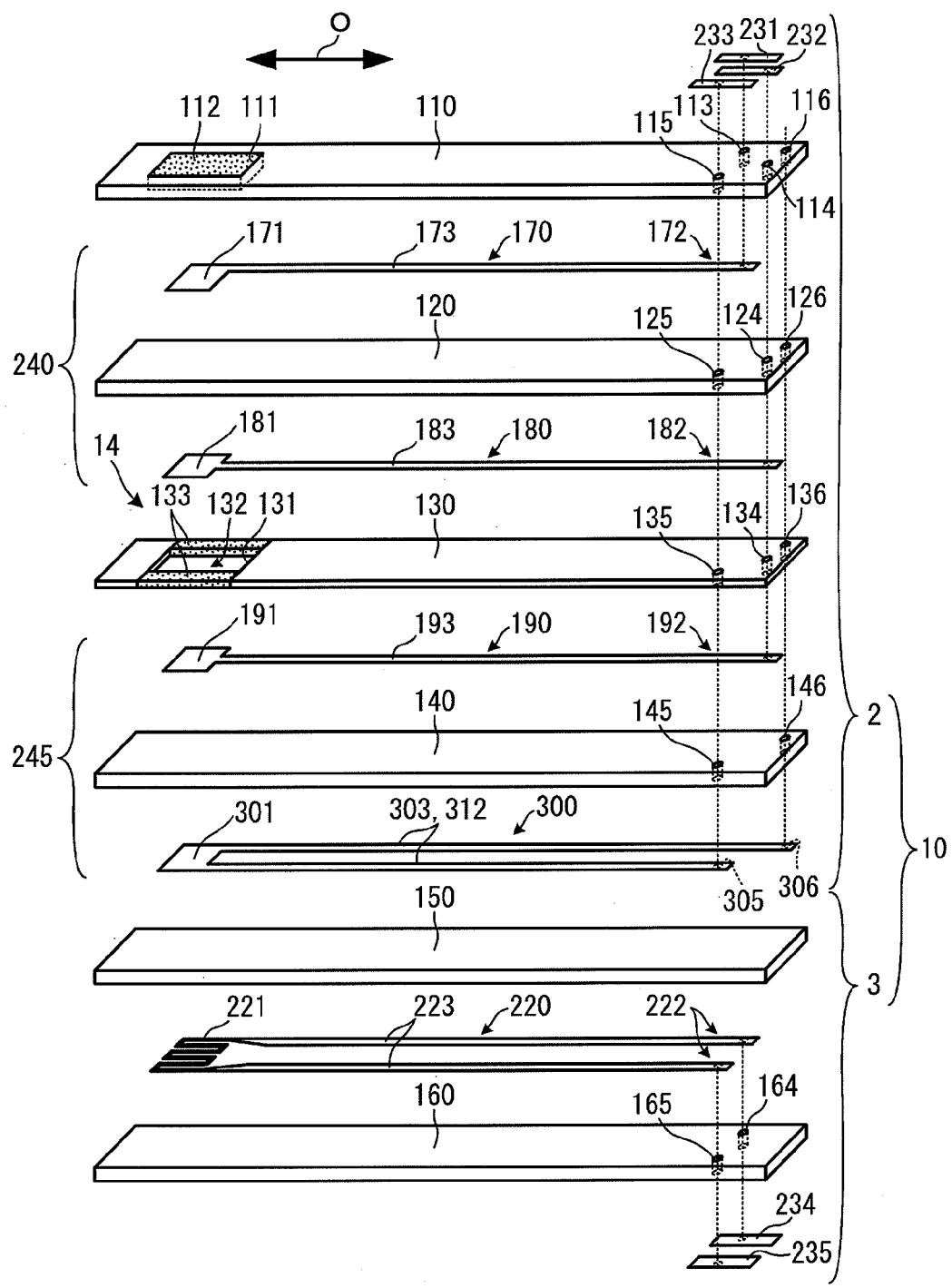
FIG. 9 is an exploded perspective view of a sensor element 10 in a modified example.
Figure 10:
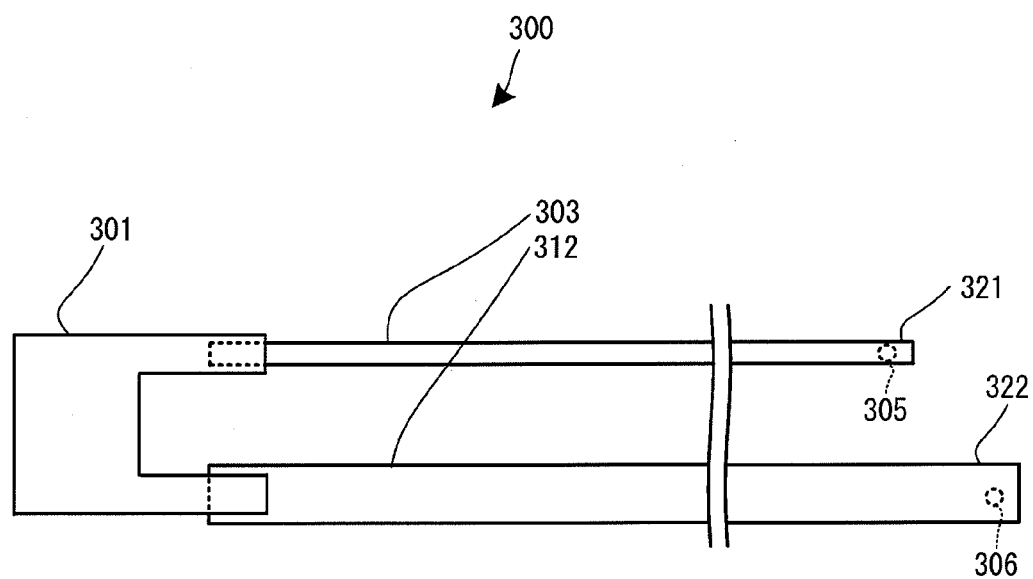
FIG. 10 is a plane view of the electric current conduction pattern 300 seen from the rear side in a modified example.

As shown in FIGS. 9 and 10, in the sensor element 10 of the oxygen sensor 1 according to the present modified example, in the rear end portions of the insulation base body 110, the solid electrolyte body 120, insulation base body 130 and the solid electrolyte body 140, through holes 116, 126, 136 and 146 consecutively penetrating in the thickness direction are formed, respectively. Moreover, the through holes 116, 126, 136 and 146 are provided at positions that do not overlap the electrode pads 231, 232 and 233, and through hole conductors are not formed therein.

In addition, the rear end portion 321 of the electrode conduction pattern 300 (more specifically, the lead portion 303) is connected to the through holes 145 by a through hole connection portion 305. That is, the electrode conduction pattern 300 is connected to the electrode pad 233 via the though hole conductors formed in the through holes 115, 125, 135 and 145. On the other hand, the rear end portion 322 of the porous portion 312 is connected to the through hole 146 by a through hole connection portion 306 situated at the main surface side of the rear end portion 322. That is, the porous portion 312 communicates with the outer portion of the sensor element 10 via through holes 116, 126, 136 and 146.

Moreover, in the above-mentioned embodiments, as the gas sensor that detects the gas concentration of the specific ingredient in the gas to be measured, the case of using the oxygen sensor 1 for detecting oxygen concentration in the gas to be measured was indicated, but the present invention is not limited thereto. The present invention can be applied without particular limitation, to a gas sensor that generates a standard oxygen portion as an internal reference. For example, in an $NO_x$ sensor for detecting the $NO_x$ concentration in the gas to be detected, the lead portion of the electrode conduction pattern having the electrode portion that functions as the oxygen standard portion can be made with the configuration indicated in the above-mentioned embodiments or the modified example.

Moreover, in the first embodiment, the lead portion 203 and the porous portion 212 are directly connected to the through hole 145, but a part, in which the electrode portion 201 and the rear end portion 203 are formed of the same material (as in the second embodiment), may be provided without being limited thereto.

Moreover, in the first and second embodiments, in the oxygen sensor 10, which includes the gas detection chamber 132 and includes the VS cell 245 constituted by the electrode portion 191 that is exposed to the gas detection chamber 132 and the electrode portion 201 pairing therewith, the lead portions 203 and 303 and the porous portions 212 and 312 are used. However, the present invention is not limited thereto. Even in a gas sensor (e.g., a lambda sensor) which does not have a gas detection chamber and in which one electrode portion is exposed to the gas to be measured and the other electrode portion forms a oxygen standard portion, the present invention including the lead portion and the porous portion, can be applied.

The present application claims priority from Japanese Patent Application No. 2009-252003, which was filed on Nov. 2, 2009, and from Japanese Patent Application No. 2010-193353, which was filed on Aug. 31, 2010, the disclosures of which are herein incorporated by reference in their entirety.

What is claimed is:
1. A gas sensor comprising:
a sensor element that is configured to detect a specific gas component in a gas to be measured, the sensor element including:
a plate-shaped solid electrolyte body;
a pair of electrodes that is stacked on the solid electrolyte body at a front end of the sensor element with the solid electrolyte body interposed therebetween,
wherein the pair of electrodes includes a measurement electrode portion that is exposed to the gas to be measured, and a standard electrode portion that is disposed in an inner portion of the sensor element and functions as an oxygen standard portion by inflow of oxygen via the solid electrolyte body,
wherein a lead portion, which extends from the front end to a rear end of the sensor element along the surface of the solid electrolyte body, is connected to the standard electrode portion,
wherein the standard electrode portion is formed with a precious metal as a main ingredient and contains a ceramic,
wherein the standard electrode portion is sandwiched between the solid electrolyte body and a sintered ceramic body,
wherein the lead portion is formed of a precious metal as a main ingredient and has a ceramic content smaller than that of the standard electrode portion,
wherein a porous portion, which extends from the front end to the rear end of the sensor element along the surface of the solid electrolyte body, has a gas permeability higher than that of the lead portion, has a porosity of between 30 to 50 volume %, is formed with a ceramic as a main ingredient, and is connected to the standard electrode portion, and
wherein, by conducting current between the measurement electrode portion and the standard electrode portion, oxygen in the gas to be measured is transferred from the measurement electrode portion side to the standard electrode portion side via the solid electrolyte body; and
a heater, wherein the heater includes a heating resistor sandwiched between a rear surface of a first insulation base body and a main surface of a second insulation base body, wherein the sensor element is stacked on the heater, and the heater is stacked on the standard electrode portion, and wherein a front end side of the porous portion partially covers a rear end side of the standard electrode portion such that a part of the rear end side of the standard electrode portion is exposed.

2. The gas sensor according to claim 1,
wherein the porous portion has a gas permeability higher than that of the standard electrode portion.

3. The gas sensor according to claim 1,
wherein the porous portion is stacked on the lead portion along a stacking direction of the pair of electrodes.

4. The gas sensor according to claim 1,
wherein the lead portion is electrically connected to an electrode pad provided on the surface of the sensor element by a through hole conductor formed in a through hole, and a part of the porous portion communicates with an outer portion of the sensor element by a through hole provided in the through hole conductor.

5. The gas sensor according to claim 1,
wherein the precious metal of the standard electrode portion is elemental platinum or an alloy of platinum with at least one selected from the group consisting of rhodium, palladium, ruthenium and gold.

6. The gas sensor according to claim 1,
wherein the lead portion and the porous portion are separate from each other and form a two row structure extending from the front end to the rear end of sensor element along the surface of the solid electrolyte body.

7. The gas sensor according to claim 6, wherein a rear end side of the lead portion is electrically connected to a through hole conductor formed in a through hole provided at the rear end of the solid electrolyte body and a rear end of the porous portion communicates with an outer portion of the sensor element via a second through hole provided at the rear end of the solid electrolyte body.

8. The gas sensor according to claim 1,
wherein the standard electrode portion is part of an electrode conduction pattern sandwiched between the solid electrolyte body and the sintered ceramic body, the electrode conduction pattern further comprising a rear end portion arranged at the rear end of the sensor element, the lead portion having a front end side connected to a rear end side of the standard electrode portion and a rear end side connected to a front end side of the rear end portion, and the porous portion having a rear end side connected to a front end side of the rear end portion.

9. The gas sensor according to claim 8, wherein the lead portion and the porous portion are not in contact with each other and form a two row structure extending from the front end to the rear end of the sensor element along the surface of the solid electrolyte body.

10. The gas sensor according to claim 8, wherein the front end side and the rear end side of the lead portion are covered by the rear end side of the standard electrode portion and the rear end portion, respectively.

11. The gas sensor according to claim 8, wherein the rear end side of the porous portion covers the rear end portion.

* * * * *